United States Patent [19]

Koop et al.

[11] Patent Number: 4,795,713
[45] Date of Patent: Jan. 3, 1989

[54] AUTO-DIGESTOR

[75] Inventors: Rodney D. Koop, Mercer Island; Thomas A. Lobb, Maple Valley; Richard L. Martin, Jr., Enumclaw, all of Wash.

[73] Assignee: The Boeing Company, Seattle, Wash.

[21] Appl. No.: 94,033

[22] Filed: Aug. 31, 1987

Related U.S. Application Data

[63] Continuation of Ser. No. 871,282, Jun. 6, 1986, abandoned.

[51] Int. Cl.$^4$ .............................................. G01N 1/00
[52] U.S. Cl. ................................... 436/175; 436/179; 436/55; 436/80; 210/766
[58] Field of Search ................. 436/175, 174, 179, 55, 436/80; 210/766

[56] References Cited

U.S. PATENT DOCUMENTS

| 1,578,666 | 3/1926 | Katz | 436/175 |
|---|---|---|---|
| 3,020,130 | 2/1962 | Ferrari | 436/175 |
| 3,322,504 | 5/1967 | Capuano | 436/175 |
| 3,846,074 | 11/1974 | Tulumello et al. | 436/175 |
| 4,397,957 | 8/1983 | Allison | 436/175 |
| 4,514,504 | 4/1985 | Rothman | 436/175 |

FOREIGN PATENT DOCUMENTS 2049085 10/1985 Japan .................................. 436/175

OTHER PUBLICATIONS

Krishnamurty et al, Trace Metal Extract . . . by Nitric Acid-$H_2O_2$, Atomic Absorption Newsletter, vol. 15, No. 3, May–Jun. '76.

Primary Examiner—David L. Lacey
Assistant Examiner—Lori-Ann Johnson
Attorney, Agent, or Firm—Bruce A. Kaser

[57] ABSTRACT

An automatic digestion system (10) is provided for digesting a continuous stream of wastewater prior to its analysis by a spectrometer system (12). The digestion system (10) includes a first metering pump (34) for drawing a continuous stream of wastewater (36) from a wastewater source (32). A second metering pump (38) draws a continuous stream of diluted nitric acid (40) from a source of acid (42) and mixes the acid with the wastewater to provide a stream of acidified wastewater (46). The acidified wastewater (46) is then heated, to digest the wastewater prior to its input into the spectrometer system (12).

1 Claim, 1 Drawing Sheet

AUTO-DIGESTOR

This application is a continuation of application Ser. No. 871,282, filed June 6, 1986, and now abandoned.

TECHNICAL FIELD

This invention generally relates to chemical treatment facilities for detoxifying and removing pollutants from manufacturing wastewater. More particularly, this invention relates to systems and/or devices that are used to monitor the effectiveness of such facilities by sampling and analyzing the waste product content of wastewater treated by the facilities.

BACKGROUND ART

Environmental considerations have dictated the implementation of various kinds of wastewater treatment facilities in the United States and throughout the world. Typically, such facilities employ chemical methods of removing potentially hazardous waste products from wastewater, thereby permitting the treated wastewater to be discharged directly into the environment by means of sewers, rivers, lakes or the like.

Given the generally toxic or polluting nature of most waste products in manufacturing wastewater, it is important to continually monitor operation of a wastewater treatment facility to ensure the facility is operating properly and is not discharging improperly treated wastewater into the environment. For this reason, it is a typical operating procedure of most treatment facilities to routinely sample and analyze treated wastewater.

It is not unusual for a wastewater sample taken for analysis to be processed in some manner prior to analysis. For example, even though a treatment facility is operating pollutants from manufacturing wastewater, there often remains a certain amount of nonharmful particulate matter in the wastewater. To conduct an accurate analysis, the particulate matter must first be "digested" prior to analysis, meaning dissolved into the wastewater.

In the past, digestion has been accomplished by manually digesting particulate matter in each of typically a large number of individual test samples. This poses a lengthy and time consuming task. The present invention provides an advantage over this and other past methods in that the present invention permits continuous and automatic digestion of a stream of sample wastewater.

DISCLOSURE OF THE INVENTION

The present invention is designed for use in conjunction with an inductively coupled plasma spectrometer. Such spectrometer is used to analyze samples of treated wastewater to make a determination as to the amount or amounts of waste products contained therein. This invention provides a continuous stream of digested wastewater to the spectrometer.

The invention includes a metering pump which is used to draw a preselected flow rate of treated wastewater from a treatment facility. This wastewater stream is then acidified, preferably, by utilizing another metering pump which draws a diluted solution of acid from a source of acid, and inputs the acid solution into the stream. The acid's concentration is such that, in combination with the flow rate drawn by the first pump, which is preselected, the acidified wastewater stream has a certain preselected pH (acid concentration level).

The acidified stream is transmitted through a conduit wherein a certain portion of which is immersed in an oil bath. The oil bath is maintained at a preselected temperature which heats the stream in the conduit. The combination of the acidification of the stream and the heating digests the stream's particulate waste products making the stream ready for analysis by the spectrometer.

BEST MODE FOR CARRYING OUT THE INVENTION

Figure 1:
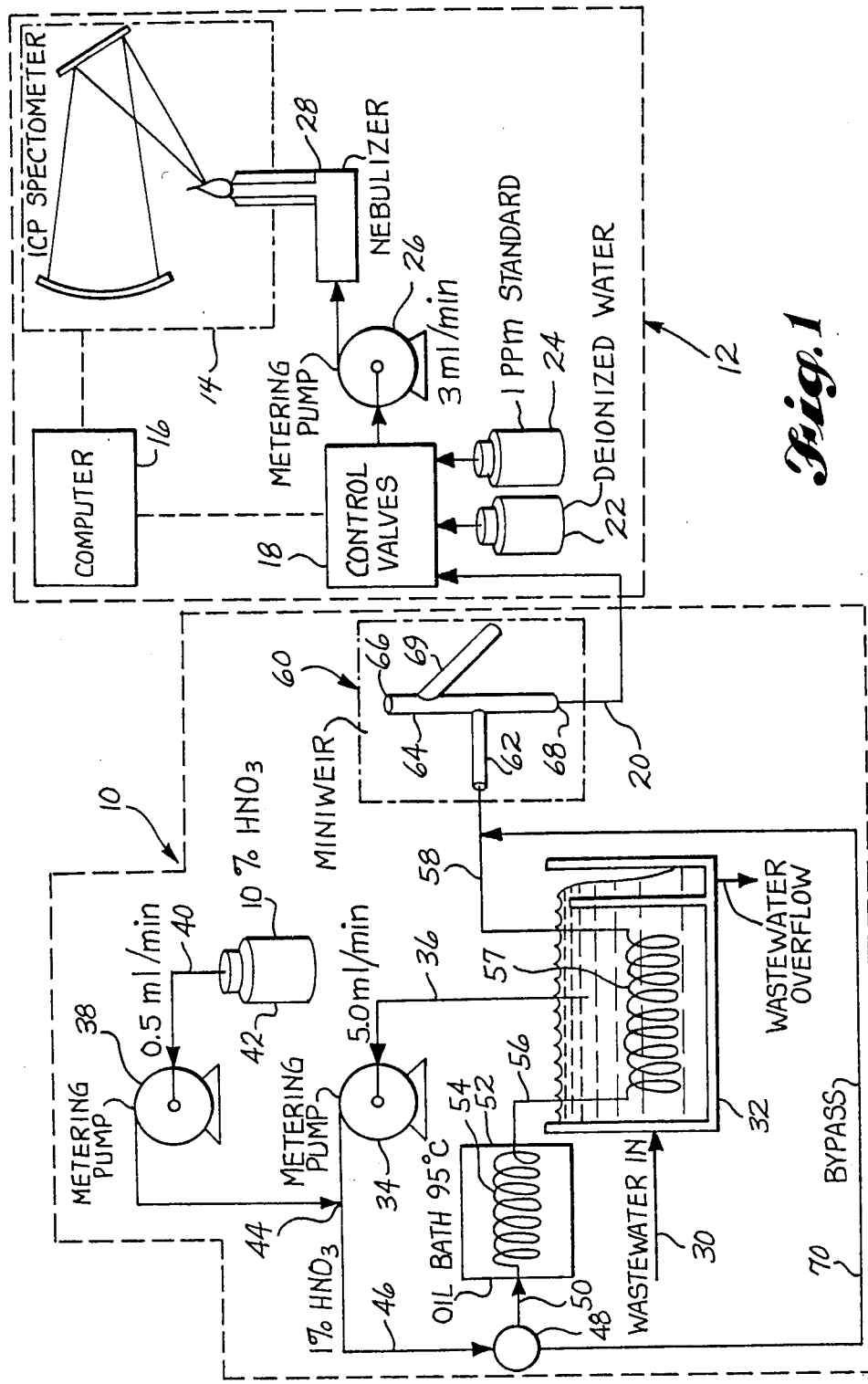
FIG. 1 is a schematic view of a preferred system constructed in accordance with the invention, for continuously digesting a wastewater stream which is used as a sample for analysis by a spectrometer system.

Referring now to the drawings, and specifically to FIG. 1, therein is shown an auto-digester, indicated generally at 10, which is blocked off by dashed lines, and which is constructed in accordance with a preferred embodiment of the invention. That portion of FIG. 1 which is blocked off by dashed lines 12 is a schematic drawing of an inductively coupled plasma spectrometer system 12. The system 12 has a spectrometer portion 14 that is controlled by a computer 16. The computer 16 also controls a valve train 18. Appropriate programming of the computer causes the valve train 18 to introduce one of either a sample wastewater stream as shown at 20, or deionized water as shown at 22, or a 1.0 ppm (parts per million) standard as shown at 24. Depending on the computer's selection, one of these items is pumped by a metering pump 26 to a nebulizer portion 28 of the spectrometer system 12.

The spectrometer system 12 as described above would be well familiar to a person skilled in the art. Such a person would know, for example, that the computer software operates to provide automatic wavelength profiling, standardization, quality control checking, alarm sounding, and wastewater analysis. By way of illustration, a spectrometer system like the system 12 is currently manufactured by the Jarrell-Ash division of Fisher Scientific of Allied Analytical in Massachusetts (Atom Comp Series 9000 model). The auto-digester 10 is designed to be added to such a machine without modification thereof. Therefore, the auto-digester 10 requires no changes in operation, equipment, or software of the spectrometer system 12.

In preferred form, the auto-digester 10 receives sample wastewater from the treatment facility as shown at 30. This stream is held in a weir box schematically indicated at 32. A first metering pump 34, or other suitable drawing means, draws the wastewater as shown at 36 from the weir box 32. Preferably, the metering pump 34 draws wastewater at a flow rate of 5.0 milliliters per minute.

A second metering pump 38, or other suitable means for acidifying the wastewater, draws a diluted solution of nitric acid ($HNO_3$) as shown at 40 from an acid reservoir 42. In preferred form, the nitric acid has an 11% by weight concentration in the reservoir 42 and is drawn from the reservoir at the rate of 0.5 milliliters per minute.

The outputs of the first and second metering pumps 34, 38 are mixed as shown at 44 to produce an acidified wastewater stream having a final concentration of 1% nitric acid. The acidified stream is then transmitted as shown at 46 to a manual control valve 48.

In preferred form, the control valve 48 is used to direct the acidified wastewater as shown at 50 into an oil bath 52. The wastewater is, of course, transmitted throughout the system 10 by conduits or similar means. A section of conduit 54, preferably shaped into a coil configuration, is immersed in the oil bath. This section 54 is of a sufficient length and has a cross section such that, in preferred form, it will take 20 minutes for the wastewater stream to pass through the oil bath and exit as indicated at 56. For example, for an acidified wastewater flow rate of 5 milliliters per minute, the conduit section may have a length of approximately 36 feet and an internal diameter of ⅛th of an inch. Digestion of the wastewater is essentially complete after heating in the oil bath 52.

After exiting the oil bath at 56, the wastewater is passed through another coil 57 which is immersed in the wastewater held by the weir box 52. This cools the heated wastewater. Then, as shown at 58, the wastewater is delivered by a conduit or the like to a tubular mini-weir assembly 60. The mini-weir 60 has a horizontal inlet portion 62, connected to the conduit 58 delivering the wastewater. It also has a vertical portion 64, connected to the inlet portion 62, with an upwardly directed end opening 66 that is located above the position where the inlet portion 62 is connected to the vertical portion. This end opening 66 is open to the atmosphere and permits debubbling of the acidified wastewater as it passes through the mini-weir 60. The vertical portion 64 also has an outlet portion 68 below the inlet portion 62 which connects the mini-weir 60 to the spectrometer system 12 as shown at 20. An overflow portion 69, connected to the vertical portion 64, below the upwardly directed end opening 66 but above the intake portion 62 thereof, provides an overflow outlet because the flow rate of the wastewater exceeds the intake capacity of the spectrometer system 12. For example, the flow rate into the spectrometer system 12, as indicated at 20, may be controlled by the metering pump 26 to a rate of 3 milliliters per minute.

The manual valve 48 may be operable to bypass the oil bath 52 as shown at 70, and deliver the acidified wastewater directly to the mini-weir 60. Occasional bypass of the oil bath is necessary when an operator of the system 10 needs a quick wastewater analysis without a twenty minute delay. It must be recognized, however, that such a quick analysis would be subject to error since the wastewater would be undigested.

The above description was provided for exemplary purposes only. It is to be appreciated that various modifications could be made to the system described above without departing from the spirit and scope of the invention. The invention is not to be limited by the above description but only by the subjoined claims in accordance with established doctrines of patent claim interpretation.

What is claimed is:

1. A method for automatically digesting a stream of wastewater prior to analysis of said wastewater, such analysis being of a type conducted for the purpose of determining the amount of certain waste products contained in said wastewater, said digestion method comprising:

drawing a continuous stream of wastewater at a preselected flow rate from a wastewater source;

acidifying said wastewater stream by continuously adding another continuous stream of only diluted nitric acid ($HNO_3$) to said wastewater stream, in an amount such that said wastewater stream has a one percent concentration of said nitric acid after addition thereof; followed by heating said wastewater stream to a temperature of 95° for 20 minutes, wherein said acidification and said heating digest said waste products in said wastewater stream.

* * * * *

UNITED STATES PATENT AND TRADEMARK OFFICE
CERTIFICATE OF CORRECTION

PATENT NO. : 4,795,713
DATED : January 3, 1989
INVENTOR(S) : Rodney Koop, Thomas Lobb and Richard Martin, Jr.

It is certified that error appears in the above-identified patent and that said Letters Patent is hereby corrected as shown below:

Column 1, line 37, following the word "operating", insert the line -- properly, i.e., the facility is adequately removing --.

Signed and Sealed this

Seventeenth Day of October, 1989

Attest:

DONALD J. QUIGG

Attesting Officer

Commissioner of Patents and Trademarks